United States Patent [19]
Challener

[11] Patent Number: 6,100,991
[45] Date of Patent: *Aug. 8, 2000

[54] NEAR NORMAL INCIDENCE OPTICAL ASSAYING METHOD AND SYSTEM HAVING WAVELENGTH AND ANGLE SENSITIVITY

[75] Inventor: William A. Challener, Grant, Minn.

[73] Assignee: Imation Corp., Oakdale, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/337,750

[22] Filed: Jun. 22, 1999

Related U.S. Application Data

[62] Division of application No. 08/915,057, Aug. 20, 1997, Pat. No. 5,955,378.

[51] Int. Cl.⁷ .................................................. G01N 21/55
[52] U.S. Cl. ............................................................. 356/445
[58] Field of Search .............................................. 356/445

[56] References Cited

U.S. PATENT DOCUMENTS

| | | |
|---|---|---|
| 4,877,747 | 10/1989 | Stewart ................................. 436/525 |
| 4,997,278 | 3/1991 | Finlan et al. ............................ 356/445 |
| 5,210,404 | 5/1993 | Cush et al. .............................. 250/216 |
| 5,322,798 | 6/1994 | Sadowski ................................ 356/445 |
| 5,341,215 | 8/1994 | Seher ...................................... 356/445 |
| 5,351,127 | 9/1994 | Kinet et al. ............................. 356/445 |
| 5,491,556 | 2/1996 | Stewart et al. .......................... 356/445 |
| 5,508,809 | 4/1996 | Peacock et al. ........................ 356/445 |
| 5,907,408 | 5/1999 | Naya et al. .............................. 356/445 |

*Primary Examiner*—Frank G. Font
*Assistant Examiner*—Zandra V. Smith
*Attorney, Agent, or Firm*—Eric D. Levinson

[57] ABSTRACT

A method and system for optically assaying a substance in a sample using a sensing system having a diffraction grating sensor. A system and method are described that expose the sensor with a light beam at near normal angles of incidence and quantitatively measure the concentration of targeted substance by determining the angular separation between resulting anomaly angles. The present invention also contemplates a system and method that quantitatively measure the concentration of targeted substance by determining the wavelength separation between resulting anomaly wavelengths. Advantages of the present invention include increased sensitivity and less susceptibility to system drifts due to mechanical motion and thermal changes than conventional diffraction grating sensors.

31 Claims, 6 Drawing Sheets

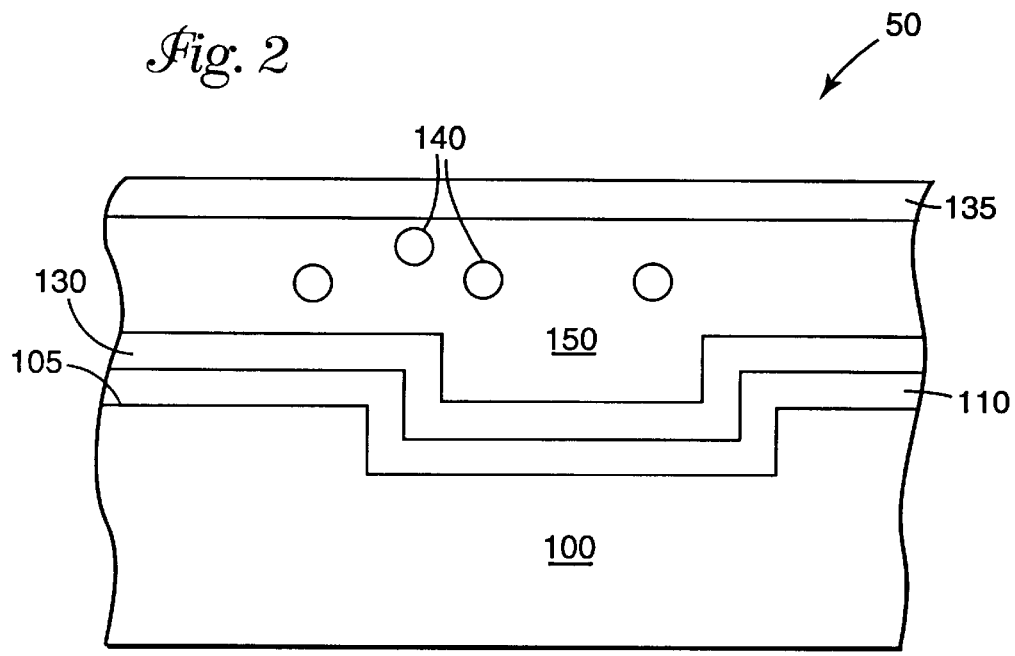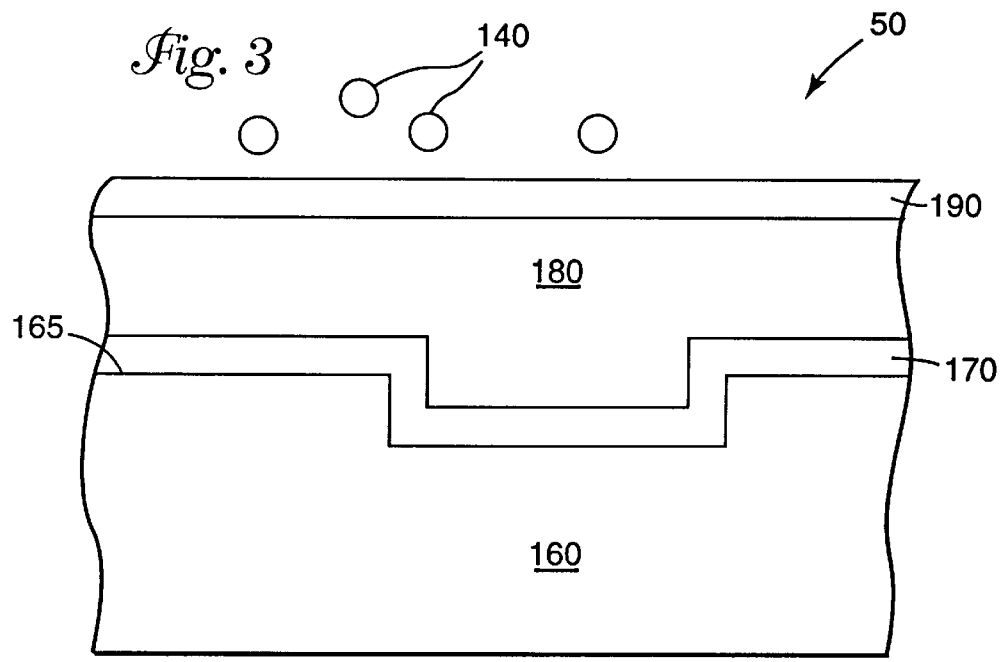

— n=1.4, λ=782.5
---------- n=1.59, λ=782.5
— — — n=1.59, λ=788

— n=1.4
----- n=1.59

NEAR NORMAL INCIDENCE OPTICAL ASSAYING METHOD AND SYSTEM HAVING WAVELENGTH AND ANGLE SENSITIVITY

This application is a Div. of Ser. No. 08/915,057 filed Aug. 20, 1997 now U.S. Pat. No. 5,955,378.

FIELD OF THE INVENTION

This invention relates generally to the field of optical sensing and, more particularly, to a method and apparatus for assaying chemical and biological materials.

BACKGROUND OF THE INVENTION

Recently, extremely sensitive optical sensors have been constructed by exploiting an effect known as surface plasmon resonance (SPR). These sensors are capable of detecting the presence of a wide variety of materials in concentrations as low as picomoles per liter. SPR sensors have been constructed to detect many biomolecules including dinitrophenyl, keyhole limpet hemocyanin, $\alpha$-Feto protein, IgE, IgG, bovine and human serum albumin, glucose, urea, avidin, lectin, DNA, RNA, hapten, HIV antibodies, human transferrin, and chymotrypsinogen. Additionally, SPR sensors have been built which detect chemicals such as polyazulene and various gases including halothane, tricloroethane and carbon tetrachloride.

An SPR sensor is constructed by sensitizing a surface of a substrate to a specific substance. Typically, the surface of the substrate is coated with a thin film of metal such as silver, gold or aluminum. Next, a monomolecular layer of receptive material, such as complementary antigens, is covalently bonded to the surface of the thin film. In this manner, the thin film is capable of interacting with a predetermined chemical, biochemical or biological substance. When an SPR sensor is exposed to a sample that includes the targeted substance, the substance attaches to the receptive material and changes the effective index of refraction at the surface of the sensor. Detection of the targeted substance is accomplished by observing the optical properties of the surface of the SPR sensor.

The most common SPR sensor involves exposing the surface of the sensor to a light beam through a glass prism. At a specific angle of incidence, known as the resonance angle, a component of the light beam's wavevector in the plane of the sensor surface matches a wavevector of a surface plasmon in the thin film, resulting in very efficient energy transfer and excitation of the surface plasmon in the thin film. As a result, at the resonance angle the amount of reflected light from the surface of the sensor changes. Typically, a sharp attenuation or amplification is exhibited and the resonance angle of a SPR sensor can be readily detected. When the targeted substance attaches to the surface of the sensor, a shift in the resonance angle occurs due to the change in the refractive index at the surface of the sensor. A quantitative measure of the concentration of the targeted substance can be calculated according to the magnitude of shift in the resonance angle.

SPR sensors have also been constructed using metallized diffraction gratings instead of prisms. For SPR grating sensors, resonance occurs when a component of the incident light polarization is perpendicular to the groove direction of the grating and the angle of incidence is appropriate for energy transfer and excitation of the thin metal film. As with prism-based sensors, a change in the amount of light reflected is observed when the angle of incidence equals the resonance angle. Previous SPR grating sensors have incorporated square-wave or sinusoidal groove profiles.

Current SPR sensors must precisely measure an absolute shift in the resonance angle in order to accurately calculate substance concentration. One inherent deficiency with this technique is that slight mechanical changes in the sensor affect the angle of incidence, thereby leading to false resonance shifts. Additionally, any slight deviation in the wavelength of the incident light may cause a shift in resonance angle and lead to faulty results. Furthermore, conventional SPR sensors are designed for a large angle of incidence, such as 45°, requiring multiple windows for transmission of light. For the reasons stated above, and for other reasons stated below which will become apparent to those skilled in the art upon understanding the present invention, there is a need in the art for a compact surface plasmon resonance sensor having improved sensitivity and less susceptibility to system variations.

SUMMARY OF THE INVENTION

In one embodiment, the invention is a system for assaying a substance in a sample using a diffraction grating sensor sensitized for the substance in the sample. A light source exposes the sensor with a light beam over a first and second range of incident angles. Angles of the first range are positive from a normal to the surface of the sensor while angles of the second range are negative from the normal. The system includes a detector that is responsive to light reflected from the sensor for each angle of the first plurality of incident angles and for each angle of the second plurality of incident angles. A controller is coupled to the detector for calculating a measure of the substance in the sample as a function of an angular separation between an angle of the first plurality of incident angles at which a first change in the reflected light is detected and an angle of the second plurality of incident angles at which a second change in the reflected light is detected.

The light source of the system may be a laser source and the system may include a beamsplitter for dividing the light beam into a first light beam and a second light beam and directing the first light beam to the sensor. The system may further include a lens for collecting the light reflected from the sensor and directing the reflected light to the detector.

The sensor may comprise a substrate having a surface formed in a groove profile, thin metal layer formed outwardly from the substrate, and a sensitizing layer formed outwardly from the thin metal layer. The sensitizing layer may include a layer of antigens. In addition, a glass window may be used to allow the light beam to pass to the receptive layer at angles of incidence substantially normal to the substrate. The groove profile may be periodic and the profile may be sinusoidal, trapezoidal, triangular or a more complicated function.

In another embodiment, the light source may be a wavelength-tunable laser source and the controller may be coupled to the detector and the laser source, such that the controller sets the wavelength of the light beam by tuning the laser source. Furthermore, the controller may tune the laser source such that an angular separation between an anomaly angle of the first plurality of incident angles and an anomaly angle of the second plurality of incident angles remains constant when the sensor is exposed to the sample. The controller calculates a measure of the substance in the sample as a function of the tuned wavelength.

In another embodiment, a sensing system includes a sensor having a first structure capable of exhibiting a diffraction anomaly, and a second structure capable of exhibiting a diffraction anomaly, the second structure being proximate to the first structure. A light source exposes the first structure of the sensor with a light beam over a plurality of incident angles such that light reflected from the first structure of the sensor is incident upon the second structure of the sensor. A detector is responsive to light reflected from the second structure of the sensor. A controller is coupled to the detector for determining an anomaly angle for the first structure of the sensor and an anomaly angle for the second structure of the sensor. The controller calculates a measure of the substance in the sample as a function of a shift in either the anomaly angle of the first grating of the sensor or the anomaly angle of the second grating of the sensor.

Furthermore, the first structure may be sensitized to the substance of the sample while the second structure of the sensor is insensitized to interaction with the sample. The light source may be a wavelength-tunable laser source and the controller may tune the wavelength of the light beam based on the anomaly angle of the second structure of the sensor. In this manner, the anomaly angle of the second structure provides a reference for the controller.

In another embodiment, the invention is a method for assaying a substance in a sample using a surface plasmon resonance sensor having a diffraction grating surface. The method includes the steps of exposing the sensor a first time with a light beam over a plurality of incident angles, detecting at least two anomaly angles during the first exposing step, interacting the sensor with the sample, exposing the sensor a second time with a light beam over the plurality of incident angles, detecting at least two anomaly angles during the second exposing step, and determining a measure of the substance in the sample as a function of an angular separation between the anomaly angles of the first exposure step and an angular separation between the anomaly angles of the second exposure step.

The incident angles may include a first plurality of incident angles and a second plurality of incident angles, wherein the first plurality of incident angles are positive in angle from a normal to the surface of the sensor and the second plurality of incident angles are negative in angle from the normal. The step of detecting the anomaly angles of the first exposure step may include the steps of: (i) detecting light reflected from the sensor during the first exposing step for each angle of the first plurality of incident angles and for each angle of the second plurality of incident angles, and (ii) determining a first anomaly angle and a second anomaly angle, wherein the first anomaly angle is an angle of the first plurality of incident angles at which a change in reflected light is detected during the first exposing step and wherein the second anomaly angle is an angle of the second plurality of incident angles at which a change in reflected light is detected during the first exposing step. The step of detecting the anomaly angles of the second exposure step may include the steps of: (i) detecting light reflected from the sensor during the second exposing step for each angle of the first plurality of incident angles and for each angle of the second plurality of incident angles, (ii) determining a third anomaly angle and a fourth anomaly angle, wherein the third anomaly angle is an angle of the first plurality of incident angles at which a change in reflected light is detected during the second exposing step and wherein the fourth anomaly angle is an angle of the second plurality of incident angles at which a change in reflected light is detected during the second exposing step.

In another embodiment, the determining step may calculate the measure of the substance in the sample as a function of an angular separation between the first anomaly angle and the second anomaly angle and an angular separation between the third anomaly angle and the fourth anomaly angle.

In another embodiment, the light source may be a wavelength-tunable laser source and the determining step includes the steps of: adjusting the wavelength of the light beam by tuning the laser source such that an angular separation between the third anomaly angle and the fourth anomaly angle substantially equals an angular separation between the first anomaly angle and the second anomaly angle, and calculating a measure of the substance in the sample as a function of the tuned wavelength.

In another embodiment, the invention is a method for assaying a substance in a sample using a sensing system including a light source and a surface plasmon resonance sensor having a first diffraction grating and a second diffraction grating wherein light reflected from the first grating of the sensor is incident upon the second grating of the sensor. The method includes the steps of exposing the first grating of the sensor a first time with a light beam over a plurality of incident angles such that the light reflected from the first grating of the sensor is incident upon the second grating of the sensor, detecting light reflected from the second grating of the sensor, determining a first anomaly angle for the first grating of the sensor, determining a first anomaly angle for the second grating of the sensor, interacting the sensor with the sample, exposing the first grating of the sensor a second time with a light beam over a plurality of incident angles such that the light reflected from the first grating of the sensor is incident upon the second grating of the sensor, detecting light reflected from the second grating of the sensor, determining a second anomaly angle for the first grating of the sensor, determining a second anomaly angle for the second grating of the sensor, and calculating a measure of the substance in the sample as a function of a shift in either the anomaly angle of the first grating of the sensor or the anomaly angle of the second grating of the sensor. The light source may be a wavelength tunable laser source and the second grating may be insensitized to interaction with the sample such that the wavelength of the light beam is tuned based on the anomaly angle of the second structure of the sensor.

BRIEF DESCRIPTION OF THE DRAWING

FIG. 2 illustrates one embodiment of an SPR diffraction grating sensor for use with the present invention;

FIG. 3 illustrates one embodiment of a diffraction anomaly sensor having a protective dielectric layer for use with the present invention;

DETAILED DESCRIPTION

In the following detailed description, references are made to the accompanying drawings that illustrate specific embodiments in which the invention may be practiced. Electrical, mechanical and structural changes may be made to the embodiments without departing from the spirit and scope of the present invention. The following detailed description is, therefore, not to be taken in a limiting sense and the scope of the present invention is defined by the appended claims and their equivalents.

Figure 1:
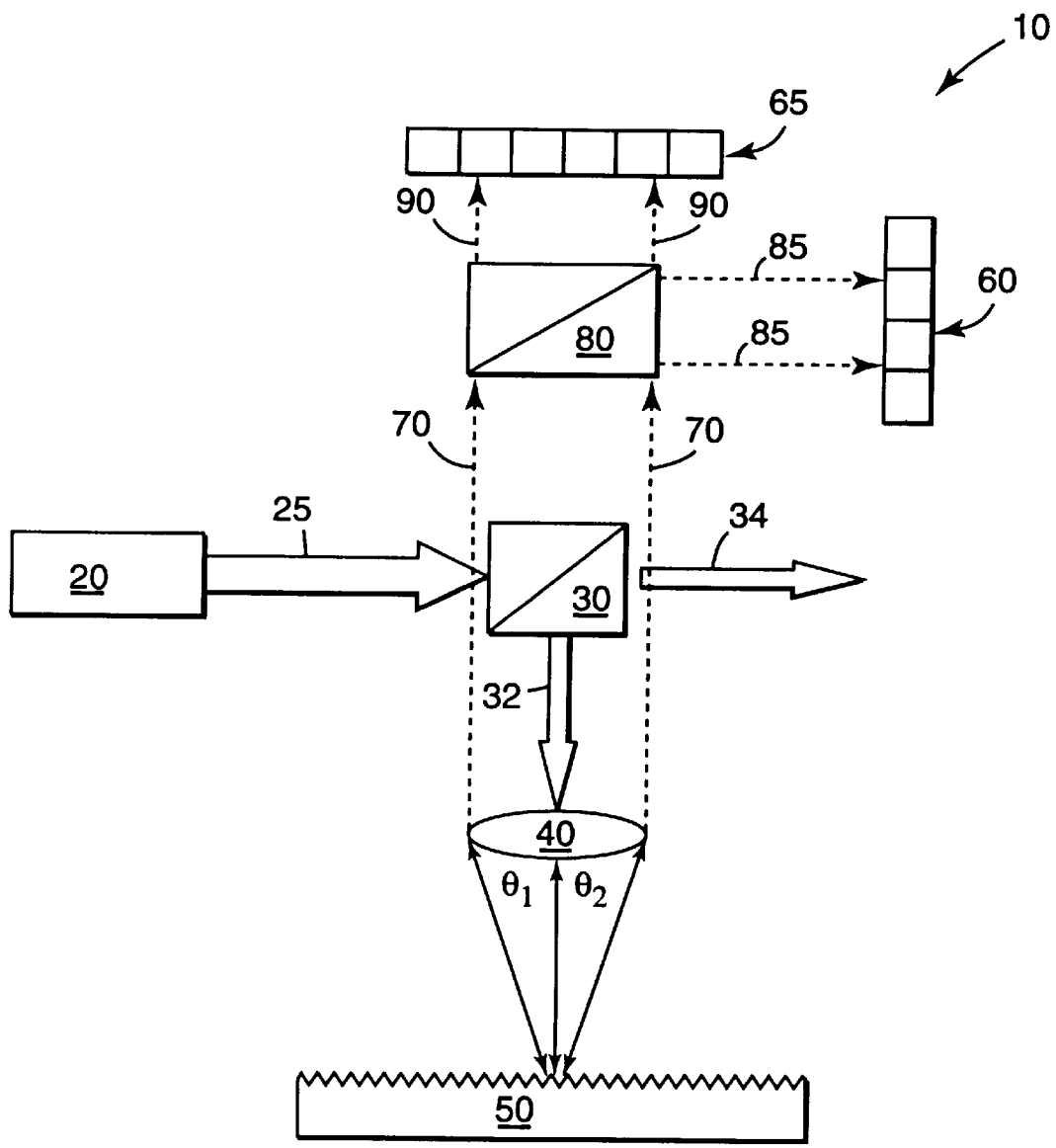
FIG. 1 illustrates one embodiment of a sensing system that detects a substance by exposing a diffraction grating sensor with light at near normal incidence and measuring a change in separation between anomaly angles.

FIG. 1 illustrates a sensing system 10 in accordance with the present invention. Referring to FIG. 1, sensing system 10 includes light source 20, beamsplitter 30, lens 40, optical sensor 50 and detector array 60. In one embodiment, sensor 50 is a surface plasmon resonance (SPR) diffraction grating sensor having a metallized diffraction grating. In another embodiment, sensor 50 is a diffraction anomaly sensor discussed in detail below. Light source 20 produces a first light beam 25 which is directed to beamsplitter 30. Preferably, light source 20 is a laser source capable of emitting a laser beam. Beamsplitter 30 divides first light beam 25 into second light beam 32 and third light beam 34. Lens 40 focuses second light beam 32 onto sensor 50 over a range of angles of incidence while third light beam 34 is unused by sensing system 10. In this sense, beamsplitter 30 and lens 40 are not critical to the invention but allow sensing system 10 to be constructed in a compact manner without requiring moving parts. For example, in another embodiment, sensor 50 is rotated along an axis normal to second light beam 32 thereby changing the angle of incidence and eliminating the need for lens 40. In another embodiment, light source 20 is rotated thereby changing the angle of incidence of second light beam 32 on sensor 50.

Sensor 50 may be designed, as detailed below, such that exposure via second light beam 32 over a range of near-normal angles results in a diffraction anomaly at both small positive and negative angles of incidence. In other words, when light beam 32 is incident upon sensor 50 at both small positive and negative angles from an axis normal to sensor 50, the zero order reflectance of sensor 50 changes. For example, although sensor 50 may be designed to work over a greater range of positive and negative angles, in one embodiment light beam 32 is directed upon sensor 50 at angles ranging up to ±20° from the normal. It is preferred, however, that light beam 32 is directed over a smaller range of angles such as up to ±10° from the normal. The positive and negative angles of incidence at which the anomaly occurs are indicated in FIG. 1 by $\theta_1$ and $\theta_2$ and will be referred to as the positive and negative anomaly angles.

When sensor 50 is exposed to a sample containing a targeted substance, the substance attaches to a surface of sensor 50 and changes the effective index of refraction at the surface of sensor 50. This corresponding change in the index of refraction shifts both anomaly angles $\theta_1$ and $\theta_2$. Thus, for a fixed wavelength of second light beam 32, the angular separation between the positive and negative anomaly angles is strongly dependent upon the amount of targeted substance present in the sample. A quantitative measure of the targeted substance can be calculated by measuring the angular separation between the anomaly angles. More specifically, after exposing sensor 50 to the sample, new anomaly angles $\theta_1$ and $\theta_2$ are determined by directing second light beam 32 to sensor 50 over a range of near-normal incidence angles. Lens 40 collects diffracted light from sensor 50 and collimates it into light beam 70 which is incident upon polarizing beamsplitter 80. Polarizing beamsplitter 80 splits light beam 70 into component 85, having a polarization vector parallel to the grooves of the surface of sensor 50, and component 90, having a polarization vector perpendicular to the grooves of the surface of sensor 50. Components 85 and 90 are incident upon detector array 60 and detector array 65, respectively.

Detector arrays 60 and 65 each include a plurality of sensing elements. A controller (not shown) monitors the sensing elements of detector arrays 60 and 65 and continuously ratios the intensities of light component 85 and light component 90 for corresponding sensing elements of detector arrays 60 and 65. In this manner, light fluctuations of the light source, or other system variations such as ripples in the sample, do not affect the calculation of the targeted species in the sample. Based on the calculated ratio for each sensing element for detector arrays 60 and 65, the controller determines the current anomaly angles $\theta_1$ and $\theta_2$ and calculates a measure of the targeted substance in the sample based on the angular separation between the anomaly angles. In another embodiment, the controller monitors anomaly angles $\theta_1$ and $\theta_2$ and sounds an alarm when the measure of the targeted substance exceed a predetermined threshold. After sensing is complete, sensor 50 may be disposed or may be washed and reused.

A particular advantage of this approach is that the sensitivity of sensing system 10 and sensor 50 is effectively twice that of conventional SPR sensors. Conventional SPR sensors measure a shift in a single resonance angle. Sensing system 10, however, by measuring the angular separation between two anomaly angles, is capable of greater precision.

Another advantage of measuring angular separation of anomaly angles $\theta_1$ and $74_2$ is that sensing system 10 is less susceptible to system drifts due to mechanical motion and thermal changes than conventional SPR sensors. Since conventional systems depend upon precise measurement of an absolute angle, any mechanical drift in the angle of incidence can result in faulty readings. By measuring the separation between anomaly angles, sensing system 10 does not depend on an absolute measurement but a "relative" measurement of anomaly angles $\theta_1$ and $\theta_2$. Therefore, the effect of mechanical drifts are substantially neutralized.

Yet another advantage of sensing system 10 is the need for only a single window (not shown) for receiving second light beam 32 from light source 20 and for allowing diffracted light 70 to escape to lens 40 and ultimately to detector array 60. Conventional SPR grating sensors are designed for a large angle of incidence, such as 45°, thereby requiring multiple windows for light passage.

In one embodiment, sensor 50 is a SPR diffraction grating sensor suitable for use with the present invention as illustrated in FIG. 2. Sensor 50 includes substrate 100 having a surface 105 formed in a groove profile. For exemplary purposes, surface 105 is illustrated as a substantially periodic square profile. Other surface profiles are contemplated including sinusoidal, trapezoidal and triangular. The period of surface 105 may range from less than 0.4 micrometers to over 2.0 micrometers. As discussed in detail below, by adjusting the period of the groove profile of surface 105, it is possible to excite the surface plasmon with light at near normal incidence, thereby causing a diffraction anomaly.

Thin metal layer 110 is formed outwardly from surface 105 of substrate 100 and comprises any suitable metal such as aluminum, gold or silver. In one embodiment, layer 110 comprises silver having a thickness of approximately 100 nm. Sensitizing layer 130 is formed outwardly from layer 110. Sensitizing layer 130 is selected to interact with a predetermined chemical, biochemical or biological substance 140 contained in sample 150. In one embodiment, sensitizing layer 130 comprises a layer of antigens capable of trapping a complementary antibody. Recently, several techniques have been developed for attaching antigens as a receptive material to layer 110 such as spin coating with a porous silica sol-gel or a hydrogel matrix. Preferably, sensitizing layer 130 is less than 100 nm thick.

Glass window 135 allows second light beam 32 to enter sensor 50 and diffracted light 70 to escape sensor 50 to lens 40 and ultimately to detector array 60. Any refraction effects caused by window 135 on second light beam 32 are minimized because second light beam 32 is substantially normal to window 135 at the air-glass interface. Additionally, it is preferable that window 135 is coated with an anti-reflection material, in order to further reduce optical effects.

When sensor 50 is a SPR diffraction grating sensor the following general equation can be used for determining the anomaly angles at which surface plasmon resonance occurs:

$$\sin\theta_{SP} = -\left(\frac{m\lambda}{n_0 p}\right)\cos\phi_{SP} \pm \sqrt{\left(\frac{n_m^2 - K_m^2}{n_0^2 + n_m^2 - K_m^2}\right) - \left(\frac{m\lambda}{n_0 p}\sin\phi_{SP}\right)^2}$$

In this equation, $\phi_{sp}$ is the azimuthal angle of second light beam 32 with respect to the grooves of surface 105, $n_o$ is the index of refraction of sample 150, $n_m + iK_m$ is the index of refraction for metal layer 110, $\lambda$ is the wavelength of second light beam 32, p is the period of the grooves of surface 105 and m is an integer. When the plane of incidence of the second light beam 32 is perpendicular to the grooves of surface 105, i.e. $\phi_{sp}$ equals 0°, the general equation can be simplified to the following equation for calculating the anomaly angles $\theta_1$ and $\theta_2$.

$$\sin\theta_{SP} = \pm\sqrt{\frac{n_m^2 - K_m^2}{n_0^2 + n_m^2 - K_m^2}} \pm \frac{m\lambda}{n_0 p}$$

In this equation, $n_o$ is the index of refraction of sample 150, $n_m + iK_m$ is the index of refraction for metal layer 110, $\lambda$ is the wavelength of second light beam 32, p is the period of the grooves of surface 105 of substrate 100, and m is an integer.

In another embodiment, sensor 50 is a diffraction anomaly sensor as illustrated in FIG. 3. Sensor 50 includes substrate 160, having a surface 165, and thin metal layer 170 which are substantially the same as in SPR grating sensor of FIG. 2. Dielectric layer 180 is formed outwardly from metal layer 170 and thereby protects metal layer 170 from oxidation and general degradation. In this manner, metal layer 170 may comprise any suitable metal and may be selected to optimize sensitivity. In one embodiment, metal layer 170 comprises silver having a thickness of approximately 100 nm. The diffraction anomaly exhibited by sensor 50 is directly affected by thickness of dielectric layer 180. It is preferable that the dielectric layer 180 has a thickness of at least 50 nm or, more preferably, at least 130 nm. In one embodiment, sensitizing layer 190 is formed outwardly from dielectric layer 180 as shown in FIG. 3. Sensitizing layer 190 is selected to interact with a predetermined chemical, biochemical or biological substance 140 contained in the sample. In another embodiment, dielectric layer 180 is selected so as to interact directly with substance 140, thereby eliminating the need for sensitizing layer 190.

Unlike conventional SPR grating sensors, diffraction anomaly sensor 50 exhibits a change in reflectivity for light polarized parallel to the grooves of surface 165. When light beam 25 has an angle of incidence equal to the diffraction anomaly angle for sensor 50, diffracted light beam 70 is not received by detector array 60 but propagates within dielectric layer 180. In this manner, dielectric layer 180 acts as a waveguide and a change in reflectivity is readily detected by the controller.

The following equations can be used to select dielectric layer 180 such that a diffraction anomaly angle, $\theta_{SP}$, occurs for component 85 having a polarization parallel to the grooves of surface 165. Using an iterative process, a wavevector for the diffraction anomaly resonance, $k_x$, can be calculated from the following equation:

$$\left(\varepsilon_1\sqrt{\varepsilon_1 k_0^2 - k_x^2} + \varepsilon_0\sqrt{\varepsilon_0 k_0^2 - k_x^2}\right)\left(\varepsilon_2\sqrt{\varepsilon_2 k_0^2 - k_x^2} + \varepsilon_1\sqrt{\varepsilon_1 k_0^2 - k_x^2}\right) + \left(\varepsilon_1\sqrt{\varepsilon_1 k_0^2 - k_x^2} - \varepsilon_0\sqrt{\varepsilon_0 k_0^2 - k_x^2}\right)\left(\varepsilon_2\sqrt{\varepsilon_2 k_0^2 - k_x^2} - \varepsilon_1\sqrt{\varepsilon_1 k_0^2 - k_x^2}\right)\exp\left(2i\sqrt{\varepsilon_1 k_0^2 - k_x^2}\,d\right) = 0$$

In this equation, $\varepsilon_o$ is the dielectric constant of the medium above the substrate, such as air or water, etc., $\varepsilon_1$ is the dielectric constant of the dielectric layer, and $\varepsilon_2$ is the dielectric constant of the metal film. Furthermore, $k_0$ is a wavevector of the incident light in vacuum and equals $2\pi/\lambda$. Finally, d is the thickness of the dielectric layer.

Once the wavevector for the diffraction anomaly resonance has been found, the following equation can be used to solve for the diffraction anomaly angle, $\theta_{SP}$:

$$\sin\theta_{SP} = -\left(\frac{m\lambda}{n_0 p}\right)\cos\phi_{SP} \pm \sqrt{\left(\frac{k_x}{n_0 k_0}\right)^2 - \left(\frac{m\lambda}{n_0 p}\sin\phi_{SP}\right)^2}.$$

In this equation, $\phi_{sp}$ is the azimuthal angle of second light beam 32 with respect to the grooves of surface 165, where 0° corresponds to the plane of incidence perpendicular to the groove direction, $n_o$ is the index of refraction of the sample, $\lambda$ is the wavelength of second light beam 32, p is the period of the grooves of surface 165, and m is an integer. Thus, a dielectric layer having a suitable dielectric constant may be readily selected so as to suppress light beam component 85 which has a polarization parallel to the grooves in surface 165 of sensor 50.

Figure 4:
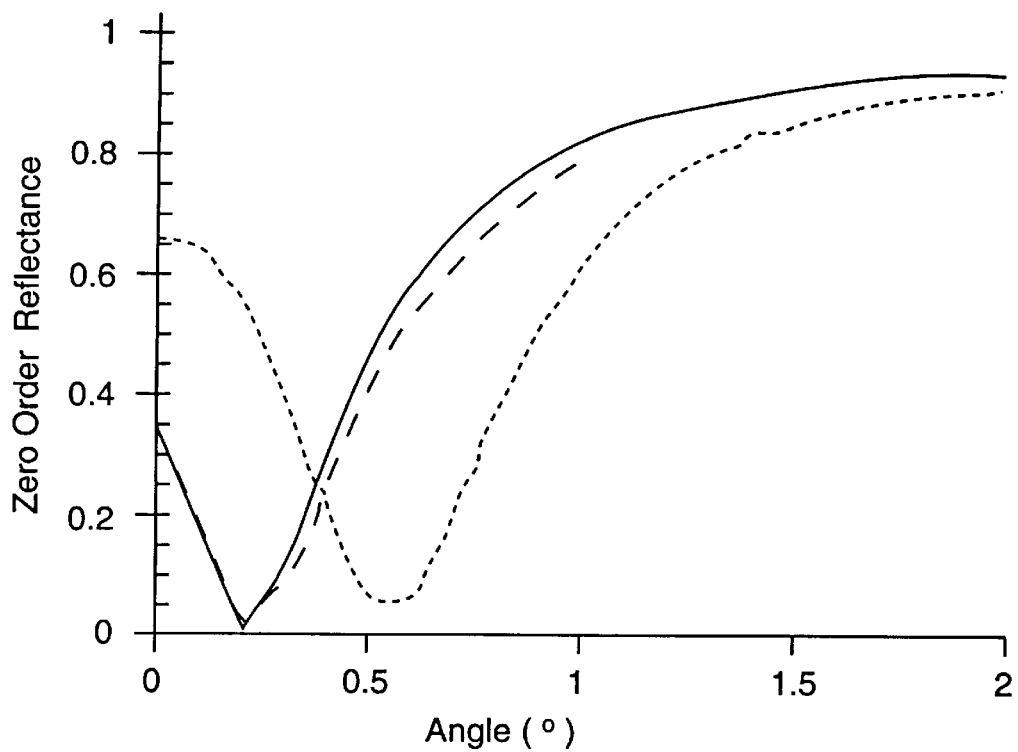
FIG. 4 graphs a calculated reflectance of a diffraction grating sensor incorporated in the sensing system of FIG. 1 for various incident angles assuming a fixed wavelength for incident light.

FIG. 4 plots the calculated reflectance of sensor 50 over a range of incidence angles for second light beam 32. More specifically, the reflectance of sensor 50 is plotted for incidence angles ranging from 0° (normal) to 2° and an azimuthal angle of 0°. Furthermore, reflectivity is plotted for various refractive indices (n) of sensitizing layer 130 of sensor 50 and for various wavelengths (λ) of second light beam 32. It is evident from FIG. 4 that at a fixed wavelength of 782.5 nm, an increase in the index of refraction of sensitizing layer 130 of sensor 50 from 1.4 to 1.59 and results in a shift of the anomaly angle by approximately 0.25 degrees.

It has been observed that diffraction grating sensors are highly dispersive in wavelength in addition to angle of incidence. The embodiments described above measure the concentration of a targeted substance by observing a shift in anomaly angle for incident light having a fixed wavelength. The concentration of a targeted substance can also be measured by observing the reflectivity of an optical sensor over a range of wavelengths of an incident light beam having a fixed angle of incidence. Under this approach, a substance may be detected by using a wavelength-tunable laser, thereby eliminating the need for moving parts to modify the angle of incidence.

Figure 5:
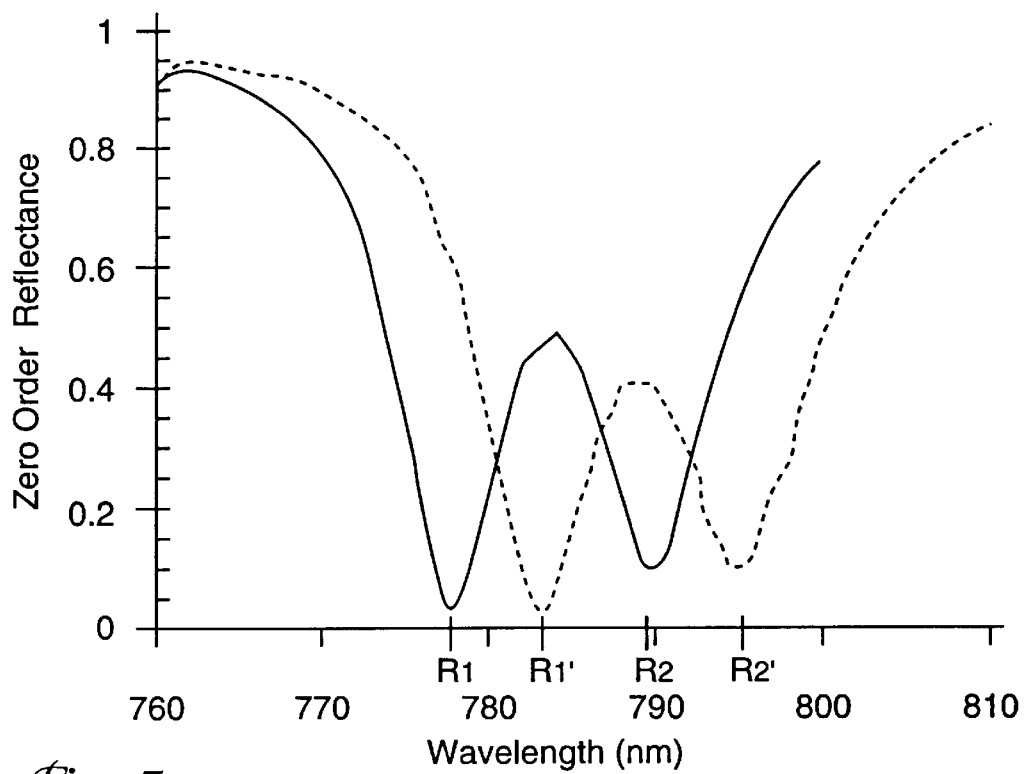
FIG. 5 graphs a calculated reflectance of a diffraction grating sensor incorporated in the sensing system of FIG. 1 over a range of wavelengths assuming a fixed incidence angle.

It has been further observed that at a fixed near-normal angle of incidence, a change in the zero order reflectance occurs at two different wavelengths. FIG. 5 plots the reflectance of a diffraction grating sensor over a range of wavelengths for an incident light beam having a fixed angle of incidence. More specifically, FIG. 5 plots reflectance versus wavelength over a range of wavelengths from 760 nm to 810 nm. Furthermore, reflectivity is plotted for various refractive indices (n). Referring to FIG. 5, at a near normal angle of incidence, a first anomaly in reflected light occurs at wavelength R1 and a second anomaly occurs at wavelength R2. An increase in the index of refraction from 1.4 to 1.5 of sensitizing layer 130 changes the wavelengths at which the first and second anomaly occur from R1 and R2 to R1' and R2', respectively. The separation in wavelength between the first and second anomalies, however, remains fixed. A quantitative measure of the targeted substance can be calculated by measuring the shift between anomaly wavelengths. As can be seen in FIG. 5, when the refractive index increases from 1.4 to 1.59, the anomaly wavelength shifts from R1 to R1', a change of approximately 5 nm which is readily detectable.

Figure 6:
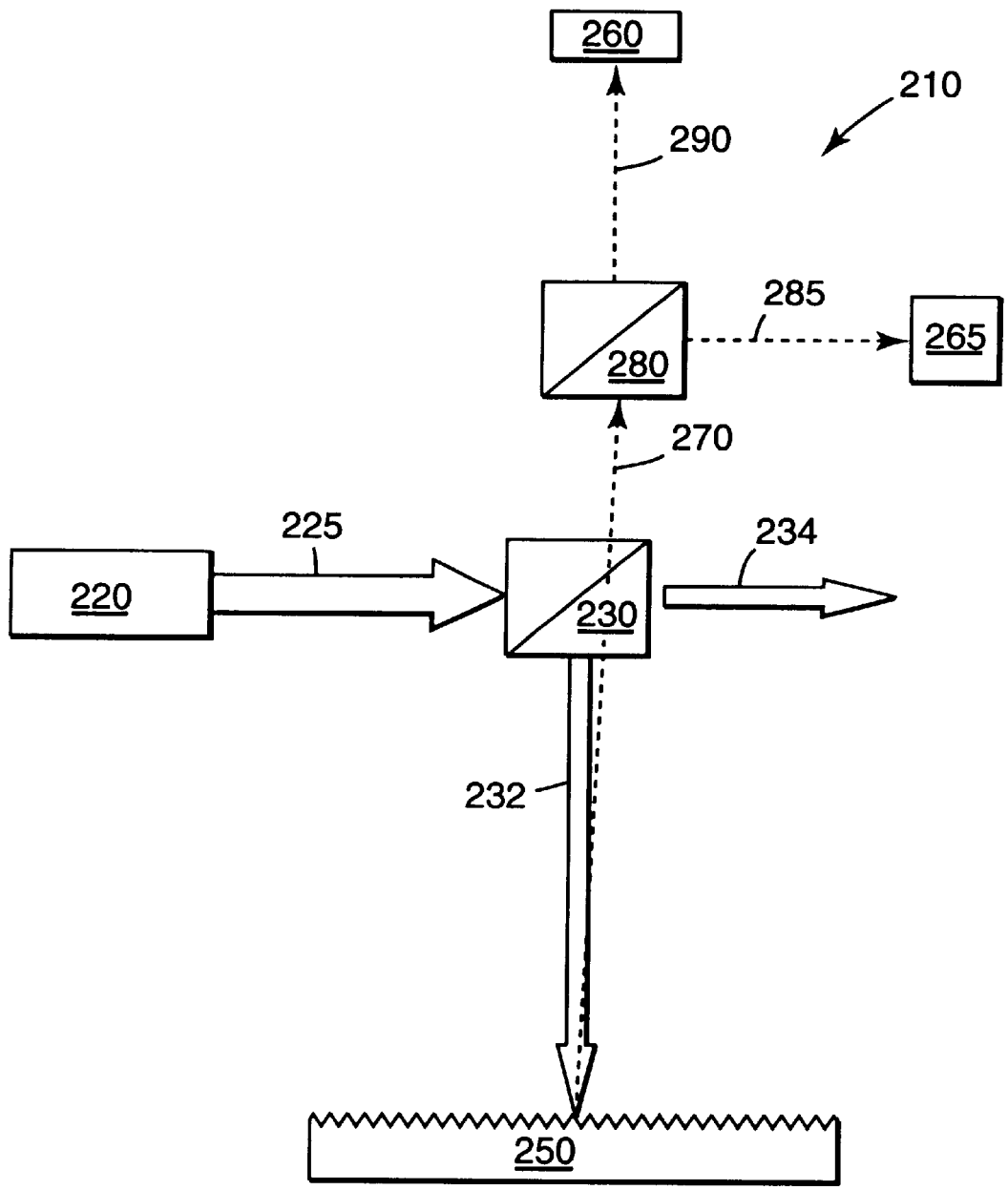
FIG. 6 illustrates one embodiment of a sensing system that detects a substance by exposing a diffraction grating sensor with light at near normal incidence and measuring a shift in anomaly wavelength.

FIG. 6 illustrates a sensing system 210 capable of sensing an absorbed substance by detecting a shift in anomaly wavelength in accordance with the present invention. Referring to FIG. 6, sensing system 210 includes light source 220, beamsplitter 230, diffraction grating sensor 250 and detector 260. Light source 220 produces light beam 225 which is directed via beamsplitter 230 toward sensor 250 at a near normal incidence angle. Beamsplitter 230 is not essential but is illustrated because it allows for sensing system 210 to be implemented in a more compact manner. Preferably, light source 220 is a wavelength tunable laser source thereby facilitating detection of wavelengths at which a diffraction anomaly occurs. Sensor 250 diffracts light beam 232 thereby producing diffracted light beam 270 incident upon polarizing beamsplitter 280. Polarizing beamsplitter 280 splits light beam 270 into component 285, having a polarization vector parallel to the grooves of the surface of sensor 250, and component 290, having a polarization vector perpendicular to the grooves of the surface of sensor 250. Components 285 and 290 are incident upon detector 265 and detector 260, respectively. Detectors 260 and 265 each produce an output signal proportional to the amount of light received.

When light source 220 is tuned such that second light beam 225 has a wavelength equal to either anomaly wavelength R1 or R2, a change in reflectivity occurs such as a very sharp attenuation or amplification in reflectivity of component 290 is observed by detector 260. As discussed above, when sensor 250 is exposed to a sample containing a targeted substance, the substance attaches to a surface of sensor 250 and changes the effective index of refraction at the surface of sensor 250. This corresponding change in the index of refraction shifts both anomaly wavelengths R1 and R2. A controller (not shown) determines the current anomaly wavelengths by controlling light source 220 to emit light over a desired range of wavelengths and monitoring the corresponding output signals from detectors 260 and 265. The controller ratios the output signals from detectors 260 and 265, determines the new anomaly wavelengths corresponding to a change in reflectivity from sensor 250 and calculates the amount of targeted substance present in the sample based on the magnitude of the shift in anomaly wavelengths.

It is contemplated that the various embodiments of the present invention discussed above can be readily combined into a single sensing system. For example, referring to FIG. 1, in another embodiment, light source 20 of sensing system 10 is a wavelength tunable semiconductor laser source thereby facilitating detection of anomaly wavelengths. As described above, before sensor 50 is exposed to the sample, the controller (not shown) directs second light beam 32 to sensor 50 over a range of near-normal incidence angles and determines the current angles of attenuation $\theta_1$ and $\theta_2$. After sensor 50 is exposed to the sample, the controller tunes the wavelength of second light beam 32 by tuning light source 20 such that the angular separation between anomaly angles $\theta_1$ and $\theta_2$ is unchanged. The controller calculates the concentration of the substance in the sample as a function of the tuned wavelength. In addition, measurement of the shift between anomaly wavelengths can also be used to insure there has been no change in the angle of incidence, or to correct for such a change in the event that a change has occurred. In this manner, the sensitivity and precision of the sensing system can be maximized.

Figure 7:
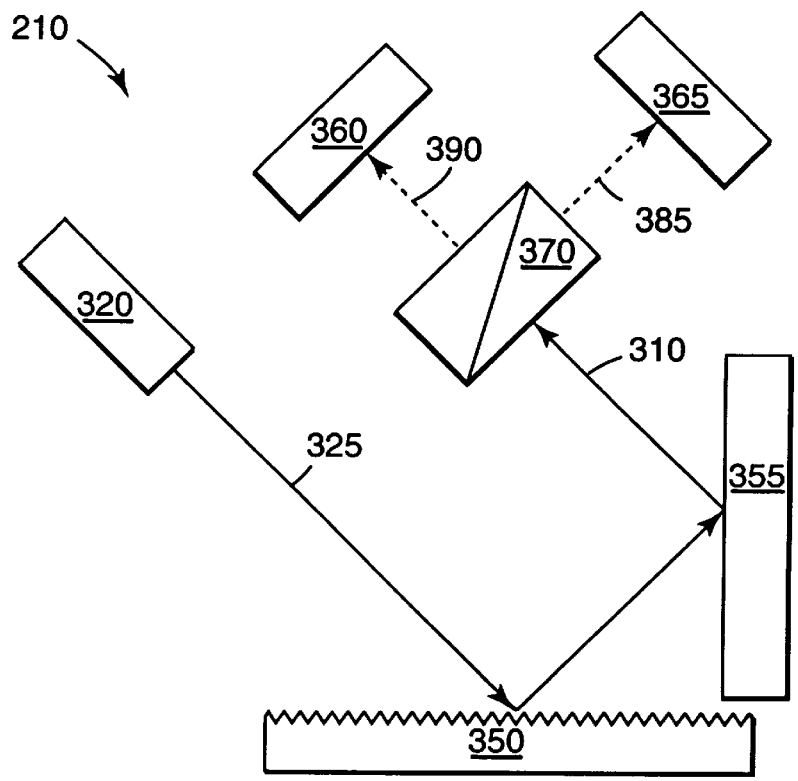
FIG. 7 illustrates one embodiment of a sensing system including a diffraction grating sensor having a double anomaly grating for eliminating effects induced by wavelength drifts.

As described above, one disadvantage of sensing systems that include optical sensors and a semiconductor laser source is the susceptibility of the system to wavelength drift due to thermal changes. FIG. 7 illustrates one embodiment of a sensing system that eliminates this effect. Referring to FIG. 7, sensing system 310 includes light source 320, first optical sensor 350, second optical sensor 355 and detector 360. Light source 320 produces light beam 325 incident on first sensor 350. Preferably, light source 320 is a wavelength tunable semiconductor laser source thereby facilitating detection of anomaly wavelengths. Light beam 325 is reflected by first sensor 350 to second sensor 355, located proximate to sensor 350, and ultimately to polarizing beamsplitter 370. Polarizing beamsplitter 370 splits light beam 310 into component 385, having a polarization vector parallel to the grooves of the surface of sensor 350, and component 390, having a polarization vector perpendicular to the grooves of the surface of sensor 350. Components 385 and 390 are incident upon detector 365 and detector 360, respectively. Detectors 360 and 365 each produce an output signal proportional to the amount of light received.

Figure 8:
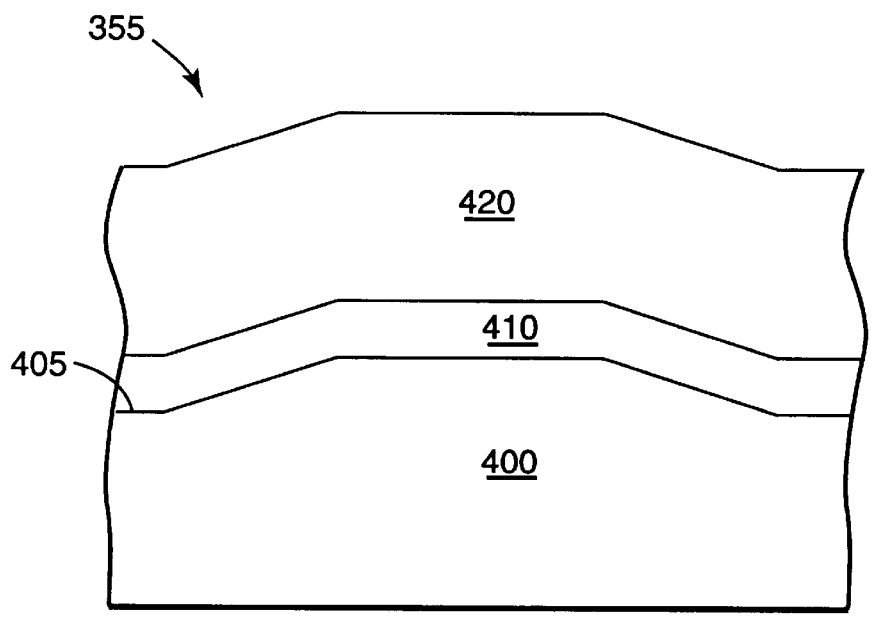
FIG. 8 illustrates one embodiment of a diffraction grating sensor having a thick dielectric layer for desensitizing the sensor to interaction with a sample.

First sensor 350 is similar to sensor 50 illustrated in FIG. 2 and described above. Second sensor 355, however, is insensitized to interaction with the sample. In one embodiment, as illustrated in FIG. 8, sensor 355 comprises substrate 400, having a surface 405 formed in a periodic trapezoidal groove profile, and thin metal layer 410 formed outwardly from surface 405. Sensor 350 further comprises dielectric layer 420 formed outward from layer 410, thereby insulating sensor 350 from interaction with the sample. Dielectric layer 420 comprises any suitable dielectric material such as silicon nitride, $Si_3N_4$, and is preferably at least 150 nm thick. In another embodiment (not shown), sensor 355 comprises substrate 400 and thin metal layer 410 and does not include a sensitizing layer or a dielectric layer. In this configuration, sensor 355 does not interact with the sample. This embodiment, however, has the disadvantage that metal layer 410 is exposed to the sample and may degrade.

Referring again to FIG. 7, as the angle of incidence of light beam 325 on sensor 350 is varied, two anomalies occur in reflected light from sensor 355. The first anomaly in reflected light occurs when the angle of incidence of light beam 325 equals the anomaly angle of sensor 350. The second anomaly occurs when the incidence angle of light reflected onto sensor 355 equals the anomaly angle of sensor 355. In this manner, sensor 350 and sensor 355 form a double anomaly grating.

The corresponding anomaly angles of sensor 350 and sensor 355 are affected by drifts in the wavelength of light beam 325. Only the anomaly angle of sensor 350, however, shifts due to interaction with the targeted substance. In addition, because the anomaly angle of SPR sensor 355 is unaffected by interaction with the sample, the anomaly angle of sensor 355 provides a reference to calibrate light source 320, thereby ensuring that light beam 325 has a wavelength substantially similar to a desired wavelength. In this manner, the effects of wavelength drift are minimized. A controller (not shown) monitors detectors 360 and 365 and continuously ratios the intensities of component 385 and component 390. Based on the ratio of intensities, the controller determines the current angles of attenuation and calculates a quantitative measure of the concentration of targeted substance by measuring the angular separation between anomaly angles.

CONCLUSION

Various embodiments of a method and system for assaying substance in a sample using a diffraction grating sensor having wavelength and angle sensitivity have been described. In one embodiment, the present invention excites a diffraction grating sensor with a light beam at small positive and negative angles of incidence (near normal) and quantitatively measures the concentration of targeted substance by determining the angular separation between resulting anomaly angles. In another embodiment, the present invention excites a diffraction grating sensor with a light beam at near normal angles of incidence and quantitatively measures the concentration of targeted substance by determining the wavelength separation between resulting anomaly wavelengths. In another embodiment, the present invention quantitatively measures the substance by tuning the wavelength such that the angular separation between anomaly angles remains constant after exposing the grating to the sample.

Several advantages of the present invention have been illustrated including increased sensitivity and less susceptibility to system drifts due to mechanical motion and thermal changes than conventional diffraction grating sensors. Furthermore, the present invention facilitates a compact diffraction grating sensor requiring a single window for light passage. In addition, the present invention allows for the construction of diffraction grating sensors that do not require a rotating member or other moving part to vary the angle of incidence.

This application is intended to cover any adaptations or variations of the present invention. It is manifestly intended that this invention be limited only by the claims and equivalents thereof.

I claim:

1. A system for assaying a substance in a sample, comprising:
    a sensor sensitized for interacting with the substance in the sample;
    a light source for exposing the sensor with a light beam over first and second pluralities of incident angles, wherein the first plurality of incident angles are positive in angle from a normal to the surface of the sensor and the second plurality of incident angles are negative in angle from the normal;
    a detector responsive to light reflected from the sensor for each angle of the first and second pluralities of incident angles; and
    a controller coupled to the first detector for calculating a measure of the substance in the sample as a function of an angular separation between an anomaly angle of the first plurality of incident angles at which a first change in reflected light is detected and an anomaly angle of the second plurality of incident angles at which a second change in reflected light is detected.

2. The system of claim 1 wherein the sensor is a surface plasmon resonance sensor having a metallized diffraction grating.

3. The system of claim 1 wherein the sensor is a diffraction anomaly sensor having a metallized diffraction grating, wherein the grating is coated with a dielectric layer for suppressing the zero order reflectance of incident light for at least one angle of incidence.

4. The system of claim 1 wherein the detector is a detector array and the light source further comprises:
    a laser source; and
    a beamsplitter for dividing the light beam into a first light beam and a second light beam, wherein the beamsplitter directs the first light beam to the sensor.

5. The system of claim 1 further comprising a lens for collecting the light reflected from the sensor and directing the reflected light to the detector array.

6. The system of claim 1 wherein the sensor further comprises:
    a substrate having a surface formed in a substantially periodic groove profile;
    a thin metal layer formed outwardly from the substrate; and
    a sensitizing layer formed outwardly from the thin metal layer.

7. The system of claim 6 wherein the detector further comprises:
    a polarizing beamsplitter for receiving the reflected light and splitting the reflected light into a first component and a second component, wherein the first component has a wave vector parallel to the grooves of the substrate and the second component has a wave vector perpendicular to the grooves of the substrate;
    a first detector for receiving the first component of the reflected light, wherein the first detector has an output signal representative of an intensity of the first component; and
    a second detector for receiving the second component of the reflected light, wherein the second detector has an output signal representative of an intensity of the second component,
    wherein the controller ratios the output signal of the first detector and the output signal of the second detector, and further wherein the controller determines the anomaly angles according the ratio of the output signals.

8. The system of claim 6 further comprising a glass window allowing the light beam to pass to the sensitizing layer at angles of incidence approximately normal to the substrate.

9. The system of claim 6 wherein the sensitizing layer comprises a layer of antigens.

10. The system of claim 6 wherein the profile is selected from the set of sinusoidal, trapezoidal and triangular.

11. A system for assaying a substance in a sample, comprising:
   a diffraction grating sensor sensitized for the substance in the sample;
   a wavelength-tunable laser source for exposing the sensor with a light beam over first and second pluralities of incident angles, wherein the first plurality of incident angles are positive in angle from a normal to the surface of the sensor and the second plurality of incident angles are negative in angle from the normal;
   a detector responsive to light reflected from the sensor; and
   a controller coupled to the detector and the laser source, wherein the controller sets the wavelength of the light beam by tuning the laser source such that an angular separation between an anomaly angle of the first plurality of incident angles and an anomaly angle of the second plurality of incident angles remains constant, and further wherein the controller calculates a measure of the substance in the sample as a function of the tuned wavelength.

12. The system of claim 11 wherein the sensor is a surface plasmon resonance sensor.

13. The system of claim 11 wherein the sensor is a diffraction anomaly sensor having a dielectric layer capable of suppressing the zero order reflectance of incident light for at least one angle of incidence.

14. The system of claim 11 further comprising a beamsplitter for dividing the light beam in to a first light beam and a second light beam, wherein the beamsplitter directs the first light beam to the sensor.

15. The system of claim 11 further comprising a lens for focusing the light beam on the sensor over the first and second plurality of incident angles and for collecting the light reflected from the sensor and directing the reflected light to the detector.

16. The system of claim 11 wherein the sensor further comprises:
   a substrate having a surface formed in a periodic groove profile;
   a thin metal layer formed outwardly from the substrate; and
   a sensitizing layer formed outwardly from the thin metal layer, the sensitizing layer capable of interacting with the substance.

17. The system of claim 16 wherein the detector further comprises:
   a polarizing beamsplitter for receiving the reflected light and splitting the reflected light into a first component and a second component, wherein the first component has a wave vector parallel to the grooves of the substrate and the second component has a wave vector perpendicular to the grooves of the substrate;
   a first detector for receiving the first component of the reflected light, wherein the first detector has an output signal representative of an intensity of the first component; and
   a second detector for receiving the second component of the reflected light, wherein the second detector has an output signal representative of an intensity of the second component,
   wherein the controller ratios the output signal of the first detector and the output signal of the second detector, and further wherein the controller determines the anomaly angles according the ratio of the output signals.

18. The system of claim 16 further comprising a window allowing the light beam to pass to the sensitizing layer at angles of incidence substantially normal to the substrate.

19. The system of claim 16 wherein the profile is selected from the set of sinusoidal, trapezoidal and triangular.

20. A system for assaying a substance in a sample, comprising:
   a sensor comprising:
      a first structure capable of exhibiting a diffraction anomaly, and
      a second structure capable of exhibiting a diffraction anomaly, the second structure proximate the first structure;
   a light source exposing the first structure of the sensor with a light beam over a plurality of incident angles such that light reflected from the first structure of the sensor is incident upon the second structure of the sensor;
   a detector responsive to light reflected from the second structure of the sensor; and
   a controller coupled to the detector for determining an anomaly angle for the first structure of the sensor and an anomaly angle for the second structure of the sensor, wherein the controller calculates a measure of the substance in the sample as a function of a shift in either the anomaly angle of the first grating of the sensor or the anomaly angle of the second grating of the sensor.

21. The system of claim 20 wherein the first structure is sensitized to the substance of the sample and the second structure of the sensor is insensitized to interaction with the sample.

22. The system of claim 20 wherein the light source is a wavelength-tunable laser source and wherein the controller tunes the wavelength of the light beam based on the anomaly angle of the second structure of the sensor.

23. The system of claim 20 wherein the first and second structures are surface plasmon resonance sensors.

24. The system of claim 20 wherein the first and second structures include a corresponding dielectric layer formed on a metal grating, the dielectric layer capable of suppressing the zero order reflectance of incident light for at least one angle of incidence.

25. The system of claim 20 wherein the first structure of the sensor further comprises:
   a substrate having a surface formed in a periodic groove profile;
   a thin metal layer formed outwardly from the substrate; and
   a sensitizing layer formed outwardly from the thin metal layer.

26. The system of claim 20 wherein the second structure of the sensor further comprises:
   a substrate having a surface formed in a periodic groove profile;
   a thin metal layer formed outwardly from the substrate; and
   a dielectric layer formed outwardly from the thin metal layer.

27. The system of claim 26 wherein the detector further comprises:

a polarizing beamsplitter for receiving the reflected light and splitting the reflected light into a first component and a second component, wherein the first component has a wave vector parallel to the grooves of the substrate and the second component has a wave vector perpendicular to the grooves of the substrate;

a first detector for receiving the first component of the reflected light, wherein the first detector has an output signal representative of an intensity of the first component; and a second detector for receiving the second component of the reflected light, wherein the second detector has an output signal representative of an intensity of the second component, wherein the controller ratios the output signal of the first detector and the output signal of the second detector, and further wherein the controller determines the anomaly angles according the ratio of the output signals.

28. The system of claim 26 wherein the groove profile is selected from the set of sinusoidal, trapezoidal and triangular.

29. A method for assaying a substance in a sample using a sensing system including a sensor having a diffraction grating and a wavelength-tunable laser source, the method comprising the steps of:

activating the laser source to provide a light beam having a tuned wavelength;

exposing the sensor a first time with a light beam over a first plurality of incident angles and a second plurality of incident angles, wherein the first plurality of incident angles are positive in angle from a normal to the sensor and the second plurality of incident angles are negative in angle from the normal;

detecting light reflected from the sensor during the first exposing step for each angle of the first plurality of incident angles and for each angle of the second plurality of incident angles;

determining a first anomaly angle and a second anomaly angle, wherein the first anomaly angle is an angle of the first plurality of incident angles at which a change of light is detected during the first exposing step and wherein the second anomaly angle is an angle of the second plurality of incident angles at which a change of light is detected during the first exposing step interacting the sensor with the sample;

exposing the sensor a second time with a light beam over the first plurality of incident angles and the second plurality of incident angles;

detecting light reflected from the sensor during the second exposing step for each angle of the first plurality of incident angles and for each angle of the second plurality of incident angles;

determining a third anomaly angle and a fourth anomaly angle, wherein the third anomaly angle is an angle of the first plurality of incident angles at which a change of light is detected during the second exposing step and wherein the fourth anomaly angle is an angle of the second plurality of incident angles at which a change of light is detected during the second exposing step; and adjusting the wavelength of the light beam by tuning the laser source such that an angular separation between the third anomaly angle and the fourth anomaly angle substantially equals an angular separation between the first anomaly angle and the second anomaly angle; and calculating a measure of the substance in the sample as a function of the tuned wavelength.

30. A method for assaying a substance in a sample using a sensing system including a light source and a sensor having a first diffraction grating and a second diffraction grating wherein light reflected from the first grating of the sensor is incident upon the second grating of the sensor, the method comprising the steps of:

exposing the first grating of the sensor a first time with a light beam over a plurality of incident angles such that the light reflected from the first grating of the sensor is incident upon the second grating of the sensor;

detecting light reflected from the second grating of the sensor;

determining a first anomaly angle for the first grating of the sensor;

determining a first anomaly angle for the second grating of the sensor;

interacting the sensor with the sample;

exposing the first grating of the sensor a second time with a light beam over a plurality of incident angles such that the light reflected from the first grating of the sensor is incident upon the second grating of the sensor;

detecting light reflected from the second grating of the sensor;

determining a second anomaly angle for the first grating of the sensor;

determining a second anomaly angle for the second grating of the sensor; and calculating a measure of the substance in the sample as a function of a shift in either the first and second anomaly angles of the first grating of the sensor or the first and second anomaly angles of the second grating of the sensor.

31. The method of claim 30 wherein the light source is a wavelength tunable laser source and the second grating is insensitized to interaction with the sample, the method further comprising the step of tuning the wavelength of the light beam based on either the first or second anomaly angle of the second structure of the sensor.

* * * * *

UNITED STATES PATENT AND TRADEMARK OFFICE
CERTIFICATE OF CORRECTION

PATENT NO.      : 6,100,991
DATED           : August 8, 2000
INVENTOR(S)     : Challener It is certified that error appears in the above-identified patent and that said Letters Patent is hereby corrected as shown below:

<u>Title page,</u>
Item [56], References Cited,
U.S. PATENT DOCUMENTS, please add:
-- 4,828,387    05/89    Sawyers
4,882,288    11/89    North
4,931,384    06/90    Layton
4,992,385    02/91    Godfrey
5,035,863    07/91    Finlan et al.
5,071,248    12/91    Tiefenthaler
5,118,608    06/92    Layton
5,310,686    05/94    Sawyers
5,478,755    12/95    Attridge
5,492,840    02/96    Malmqvist
5,583,643    12/96    Gass
5,598,267    01/97    Sambles
5,636,633    06/97    Messerschmidt
5,751,482    05/98    Challener, IV
5,776,785    07/98    Lin et al.
5,738,825    04/98    Rudigier et al. --

FOREIGN PATENT DOCUMENTS, please add:
-- 0 321 523 B1 02/92   EPO --

UNITED STATES PATENT AND TRADEMARK OFFICE
CERTIFICATE OF CORRECTION

PATENT NO.    : 6,100,991
DATED         : August 8, 2000
INVENTOR(S)   : Challener It is certified that error appears in the above-identified patent and that said Letters Patent is hereby corrected as shown below:

<u>Title page, (continued)</u>
Item [56], References Cited,
OTHER DOCUMENTS, please add:
-- "Double Excitation of a Resonant Surface Plasmon Maximum," Journal of Modern Optics, M.J. Jory, 1993, Vol. 40, No. 9, pp. 1657-1662.

"Unusual splitting behavior of the dispersion of surface polaritons in grating of different symmetry, amplitude, and profile," Applied Optics, B. Fischer, Vol. 34, No. 25, Sept. 1, 1995, pp. 5773-5779.

"Grating-Coupled Surface Plasmon for Measuring the Refractive Index of a Liquid Sample," J. Phys. D: Applied Physics, Hiroshi Kano, Vol. 34, 1995, pp. 331-335. --

Signed and Sealed this

Twelfth Day of November, 2002

*Attest:*

*Attesting Officer*

JAMES E. ROGAN
*Director of the United States Patent and Trademark Office*